US00PP26754P2

(12) United States Plant Patent
van Noort

(10) Patent No.: US PP26,754 P2
(45) Date of Patent: May 24, 2016

(54) *GERANIUM* PLANT NAMED 'NOORTVIOLET'

(50) Latin Name: *Geranium cinereum*
Varietal Denomination: Noortviolet

(71) Applicant: Marco van Noort, Warmond (NL)

(72) Inventor: Marco van Noort, Warmond (NL)

(73) Assignee: Marco van Noort Breeding BV, Warmond (NL)

( * ) Notice: Subject to any disclaimer, the term of this patent is extended or adjusted under 35 U.S.C. 154(b) by 10 days.

(21) Appl. No.: 14/544,142

(22) Filed: Dec. 2, 2014

(51) Int. Cl.
*A01H 5/02* (2006.01)

(52) U.S. Cl.
USPC ..... Plt./324

(58) Field of Classification Search
USPC ..... Plt./324
CPC ..... A01H 5/02; A01H 5/0277
See application file for complete search history.

*Primary Examiner* — Kent L Bell
(74) *Attorney, Agent, or Firm* — Penny J. Aguirre

(57) ABSTRACT

A new cultivar of *Geranium cinereum*, 'Noortviolet', that is characterized by its relatively large flowers that are clear pink with conspicuous violet centers and consistent in color throughout the plant, and its greater resistance to soil fungi relative to other *Geranium cinereum* cultivars.

2 Drawing Sheets

Botanical classification: *Geranium cinereum.*
Cultivar designation: 'Noortviolet'.

BACKGROUND OF THE INVENTION

The present invention relates to a new and distinct cultivar of *Geranium* plant, botanically known as *Geranium cinereum* 'Noortviolet' and will be referred to hereafter by its cultivar name, 'Noortviolet'.

'Noortviolet' was derived from a breeding program conducted by the Inventor in Warmond, The Netherlands. The objectives of the breeding program were to develop new cultivars of *Geranium cinereum* in a range of flower colors that commence bloom early in the season and exhibit disease resistance, compact plant habits and rain resistance. 'Noortviolet' arose from a cross made in summer of 2010 between an unnamed and unpatented plant of *Geranium cinereum* var. *subcaulescens* seedling from the Inventor's breeding program as the female parent and *Geranium cinereum* 'Laurence Flatman' (not patented) as the male parent. The Inventor selected 'Noortviolet' as a single unique plant amongst the seedlings that resulted from the above cross in May of 2012.

Asexual propagation of the new cultivar was first accomplished by in vitro propagation by the Inventor in Otrebusy, Poland in April of 2014. Asexual propagation by in vitro propagation and root cuttings has determined that the characteristics of the new cultivar are stable and are reproduced true to type in successive generations.

SUMMARY OF THE INVENTION

The following traits have been repeatedly observed and represent the characteristics of 'Noortviolet'. These attributes in combination distinguish 'Noortviolet' as a new and distinct cultivar of *Geranium.*

1. 'Noortviolet' exhibits relatively large flowers that are clear pink with conspicuous violet centers.
2. 'Noortviolet' exhibits greater resistance to soil fungi relative to other *Geranium cinereum* cultivars.

3. 'Noortviolet' exhibits flowers that are consistent in color throughout the plant.

The female parent of 'Noortviolet' differs from 'Noortviolet' in having flowers that are smaller in size, solid violet in color and less consistent in flower color. The male parent of 'Noortviolet', 'Laurence Flatman', differs from 'Noortviolet' in having flowers that are light pink in color with dark pink stripes. 'Noortviolet' can also be compared to the *Geranium cinereum* cultivar, 'Thumbling Hearts' (U.S. Plant Pat. No. 20,096). 'Thumbing Hearts' is similar to 'Noortviolet' in overall plant shape. 'Thumbling Hearts' differs from 'Noortviolet' in having flowers that are smaller in size, lighter pink in color with a slightly smaller purple center.

BRIEF DESCRIPTION OF THE DRAWINGS

The accompanying colored photographs illustrate the overall appearance and distinct characteristics of the new *Geranium*. The photographs were taken of a one year-old plant of 'Noortviolet' as field grown in Warmond, The Netherlands and placed in a container for the photographs.

The photograph in FIG. 1 provides an overall view of a plant of 'Noortviolet' in bloom.

Figure 1:
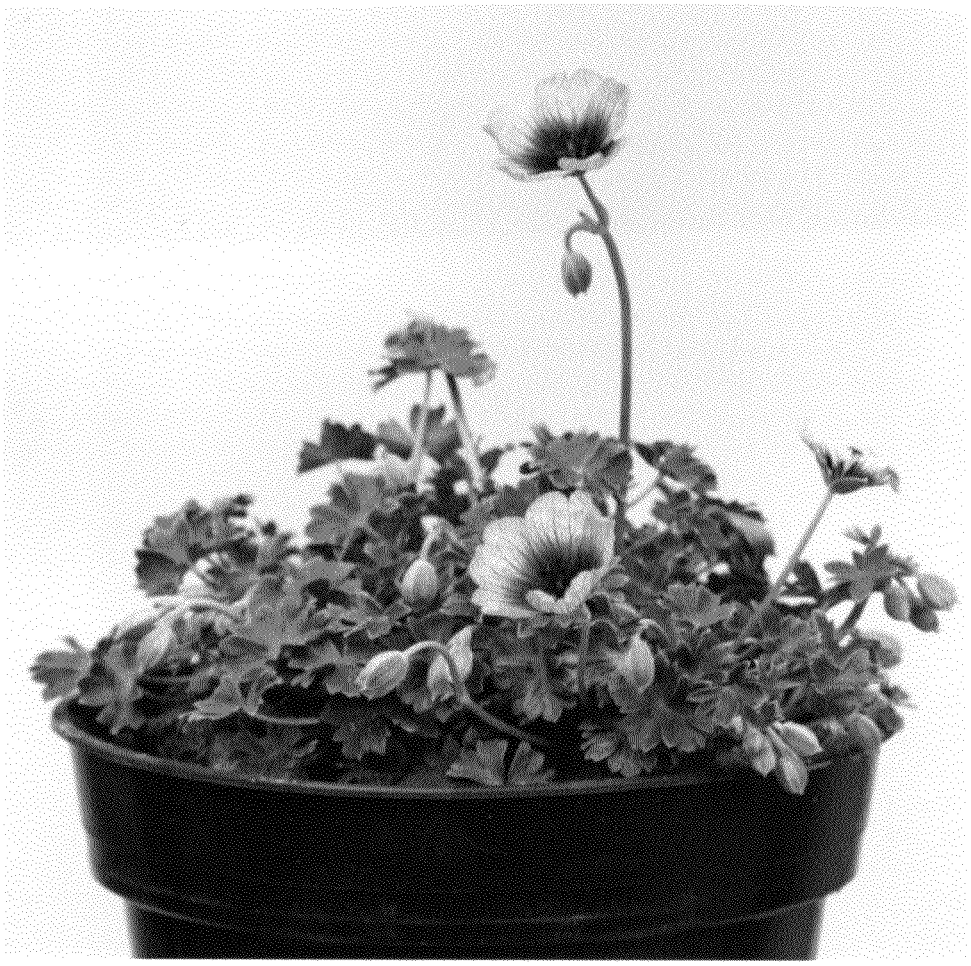
Figure 2:
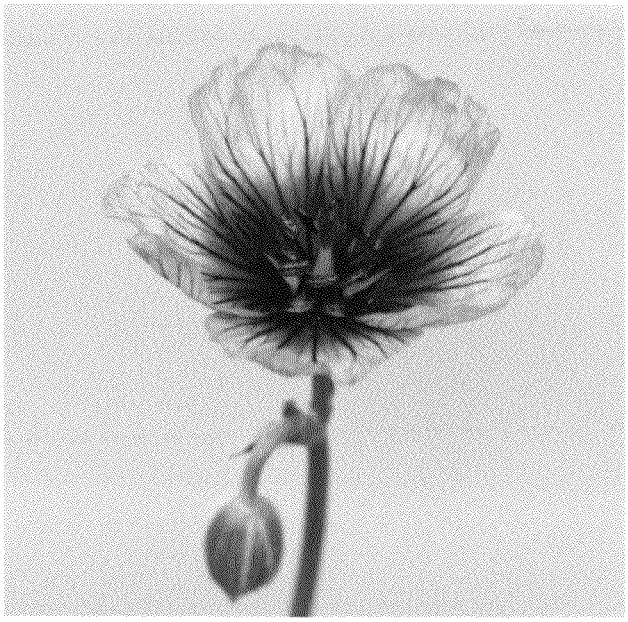

The photograph in FIG. 2 provides a close-up view of a flower of 'Noortviolet'.

Figure 3:
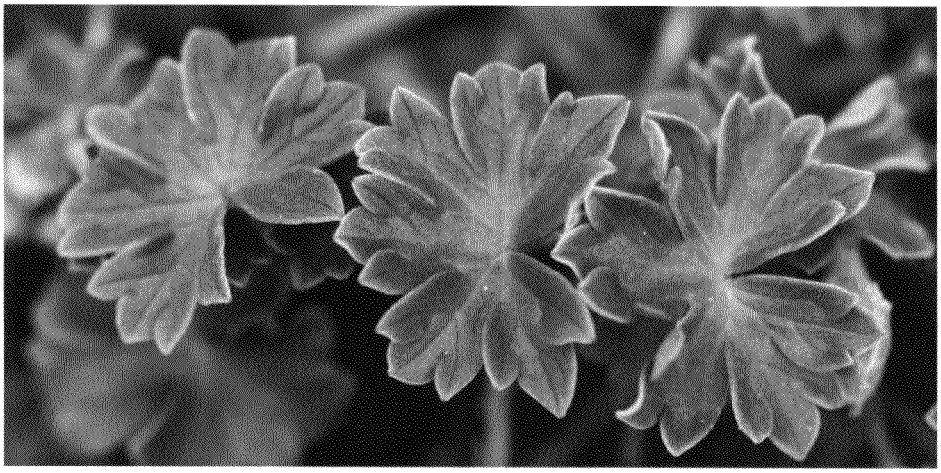

The photograph in FIG. 3 provides a close-up view of the foliage of 'Noortviolet'.

The colors in the photographs are as close as possible with the digital photography techniques available, the color values cited in the detailed botanical description accurately describe the colors of the new *Geranium.*

DETAILED BOTANICAL DESCRIPTION OF THE PLANT

The following is a detailed description of one year-old plants of the new cultivar as grown outdoors in Warmond, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—April to June in The Netherlands.

*Plant type*.—Herbaceous perennial.

*Plant habit*.—Low growing, spreading, and flattened with flowers held above the foliage.

*Height and spread*.—An average of 15 cm in height and 25 cm in spread.

*Cold hardiness*.—At least to U.S.D.A. Zone 5.

*Diseases*.—Observed to have some resistance to soil fungi caused by *Botrytis cinerea* and *Pythium* spp.

*Root description*.—Fibrous and fine, primarily N170A and N170B in color.

*Root development*.—An average of 20 weeks to fully develop from a rooted cutting in a 9-cm container.

*Growth rate*.—Moderate, about 7 cm per month in spring.

*Propagation*.—In vitro propagation (preferred) and root cuttings.

Stem description:

*Stem size*.—Average of 4.8 cm in length and 2 mm in width.

*Stem shape*.—Round.

*Stem color*.—144D, stems fade upward to 174B.

*Stem surface*.—Slightly glossy with stems densely covered with very short soft adpressed hairs; average of 0.3 mm in length and too small to measure color.

*Stem strength*.—Moderately strong.

*Internode length*.—Average of 3.5 cm.

*Branching*.—Moderately branched with an average of 11 lateral branches.

Foliage description:

*Leaf shape*.—Reniform (in outline), palmately deeply cleft to parted with an average of five lobes.

*Leaf division*.—Simple.

*Leaf base*.—Hastate (touching to slightly overlapping).

*Leaf apex*.—Broadly acute.

*Leaf venation*.—Palmate, color of upper side 144A, color of lower side 144B.

*Leaf margins*.—Palmately deeply cleft to parted into an average of five lobes, margins of lobes incised.

*Leaf attachment*.—Petiolate.

*Leaf arrangement*.—Opposite.

*Leaf surface*.—Both surfaces are slightly glossy and densely covered with short and soft adpressed hairs, average of 0.5 mm in length and too small to measure color.

*Leaf size*.—Average of 2.1 cm in length and 2.3 cm in width.

*Leaf color*.—Upper surface young; 137B, lower surface young; color between 138A and 147B, upper surface mature; color N137C to N137B, lower surface mature; 147B.

*Leaf quantity*.—Average of 4 leaves per lateral branch.

*Petioles*.—Average of 5.7 cm in length and 1.5 mm in diameter, surfaces are 144A to 144B in color, surface puberulent.

*Stipules*.—2 leafy stipules are present at the base of the leaves, narrow deltoid in shape, narrow acuminate apex, truncate base, average of 6 mm in length and 3 mm in width, color; both surfaces are 145B to 145C in color, both surfaces puberulent.

Flower description:

*Inflorescence type*.—Single, rotate flowers, arranged in pairs.

*Lastingness of flowers*.—About 7 days on the plant, sepals persistent.

*Flower size*.—Average of 1.5 cm in height and 3.4 cm in diameter.

*Flower fragrance*.—None.

*Flower number*.—Average of 8 flowers and buds per lateral stem, average of 88 per plant.

*Flower aspect*.—Upright.

*Flower buds*.—Obovate in shape, average of 9 mm in length and up to 6 mm in diameter, 138A, veined 137B, surface moderately covered with short soft adpressed hairs 0.5 mm in length and too small to measure color.

*Corolla features*.—Petals are unfused and arranged in a rotate form, slightly cupped.

*Petal number*.—5.

*Petal shape*.—Obcordate.

*Petal color*.—When opening and fully open upper surface; N74D, lower 40% of the petal is between 71A and N79C, veined N186C, when opening and fully open lower surface; between N74D and 75A, lower 40% of the petal is 71A, veined N186C.

*Petal surface*.—Upper side very slightly glossy, upper side more velvety.

*Petal margins*.—Entire except for apex.

*Petal apex*.—Retuse to emarginated.

*Petal size*.—Average of 2 cm in length and 1.7 cm in width.

*Calyx*.—Rotate and cupped, 6 mm in length and 1.6 cm in diameter.

*Sepals*.—5, ovate in shape, average of 1.1 mm length and 4.5 mm in width, entire margin, mucronate apex, cuneate base, both surfaces matte, color young and mature upper surface; 143A, color young and mature lower surface; 137C to 137D in color.

*Peduncles*.—Round in shape, average of 7.6 cm in length and 1.5 mm in diameter, strong, held at a 65° angle to the lateral branch, color 144B, upper surface (sun exposed) tinged 174C, surface puberulent.

*Pedicels*.—Round in shape, average of 1.8 mm in length and 1 mm in diameter, strong, one flower straight on top of peduncle, the second flower held in an average angle of 45° to lateral branch, color 144A, surface puberulent.

Reproductive organs:

*Gynoecium*.—1 pistil, average of 6 mm in length, 5 stigmas are decurrent (reflexed) and N186C in color, style is an average of 4 mm in length and 143A in color, ovary is 144A in color.

*Androecium*.—10 stamens, anthers are dorsifixed, oblong in shape and held at a 90° angle on top of filament, 2.5 mm in length, and 203B to 203C in color, filaments are 6 mm in length and a color between N186C and 200A, pollen is low in quantity and 11A in color.

*Fruit/seeds*.—None observed.

It is claimed:

1. A new and distinct cultivar of *Geranium* plant named 'Noortviolet' as herein illustrated and described.

* * * * *